United States Patent
Zhang et al.

(10) Patent No.: US 9,814,412 B2
(45) Date of Patent: Nov. 14, 2017

(54) METHOD AND DEVICE FOR DETERMINING A BLOOD CONSTITUENT

(71) Applicant: Fresenius Medical Care Deutschland GmbH, Bad Homburg (DE)

(72) Inventors: Wei Zhang, Niederwerrn (DE); Christoph Bardorz, Rottendorf (DE); Carsten Mueller, Euerbach (DE); Elke Schulte, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 772 days.

(21) Appl. No.: 13/685,198

(22) Filed: Nov. 26, 2012

(65) Prior Publication Data

US 2013/0144139 A1   Jun. 6, 2013

Related U.S. Application Data (60) Provisional application No. 61/565,525, filed on Dec. 1, 2011.

(30) Foreign Application Priority Data

Dec. 1, 2011  (DE) .................... 10 2011 119 824

(51) Int. Cl.
*A61B 5/1455* (2006.01)
*A61B 5/145* (2006.01)
(Continued)

(52) U.S. Cl.
CPC ...... *A61B 5/14525* (2013.01); *A61B 5/14557* (2013.01); *A61M 1/3609* (2014.02);
(Continued)

(58) Field of Classification Search
None
See application file for complete search history.

(56) References Cited

U.S. PATENT DOCUMENTS

2004/0067594 A1   4/2004   Mori et al.
2012/0031841 A1   2/2012   Zhang

FOREIGN PATENT DOCUMENTS

DE   10 2009 017 304 A1   10/2010
DE   10 2010 026 723.6     1/2012
(Continued)

OTHER PUBLICATIONS

PCT International Search Report and Written Opinion from PCT/EP2012/004762, dated Feb. 18, 2013.
(Continued)

*Primary Examiner* — Eric Winakur
*Assistant Examiner* — Marjan Fardanesh
(74) *Attorney, Agent, or Firm* — Kilyk & Bowersox, P.L.L.C.

(57) ABSTRACT

A method and device for determining the concentration of blood constituents, in particular haemoglobin, in a hose line of an extracorporeal blood circuit of an extracorporeal blood treatment apparatus, and an extracorporeal blood treatment apparatus with a device for determining the concentration of a blood constituent, are based on the correction of the influence of the blood flow rate of the blood flowing through the hose line on the determination of the concentration of the blood constituent. The device comprises a computing and evaluation unit configured such that a correction factor is ascertained for the influence of the blood flow rate on the determination of the concentration of the blood constituent. The concentration of the blood constituent is then determined based on a relationship describing the dependence of the concentration of the blood constituent on the intensity of the decoupled electromagnetic radiation, taking account of the correction factor.

31 Claims, 3 Drawing Sheets

(51) Int. Cl.
    *G01N 21/85* (2006.01)
    *G01N 21/53* (2006.01)
    *A61M 1/36* (2006.01)

(52) U.S. Cl.
    CPC ............ *G01N 21/53* (2013.01); *G01N 21/85* (2013.01); *A61M 2205/3313* (2013.01)

(56) References Cited

FOREIGN PATENT DOCUMENTS

| | | |
|---|---|---|
| EP | 0 074 428 A1 | 3/1983 |
| EP | 0 575 712 A2 | 12/1993 |
| WO | 2004/057313 A1 | 7/2004 |
| WO | 2008/000433 A1 | 1/2008 |
| WO | 2010/115621 A3 | 10/2010 |

OTHER PUBLICATIONS

International Preliminary Report on Patentability (IPRP) and Written Opinion in PCT/EP2012/004762, dated Jun. 3, 2014.

|  |  | ΔHb [g/dl] | | | | | |
| :---: | :---: | :---: | :---: | :---: | :---: | :---: | :---: |
| Hb [g/dl] | ΔQ$_b$ 300 ml/min | I | | | II | | |
|  |  | Min | Mean | Max | Min | Mean | Max |
| 15,80 | ±100 | 0,00091 | 0,01317 | 0,04951 | 0,02214 | 0,08034 | 0,13044 |
|  | ±200 | 0,00904 | 0,11274 | 0,31543 | 0,04136 | 0,17523 | 0,26758 |
| 12,83 | ±100 | 0,04077 | 0,35638 | 0,79041 | 0,01240 | 0,02612 | 0,04429 |
|  | ±200 | 0,16609 | 0,23232 | 0,31783 | 0,00854 | 0,02513 | 0,04889 |
| 10,43 | ±100 | 0,08963 | 0,10340 | 0,12491 | 0,00308 | 0,01873 | 0,02570 |
|  | ±200 | 0,17233 | 0,19991 | 0,24176 | 0,00455 | 0,01752 | 0,03397 |
| 8,30 | ±100 | 0,03910 | 0,05364 | 0,07108 | 0,00531 | 0,01682 | 0,04879 |
|  | ±200 | 0,07486 | 0,10186 | 0,14004 | 0,02041 | 0,04366 | 0,07803 |
| 7,04 | ±100 | 0,01579 | 0,02528 | 0,04360 | 0,00887 | 0,03042 | 0,05252 |
|  | ±200 | 0,01194 | 0,04932 | 0,08768 | 0,01370 | 0,06004 | 0,10835 |

Fig. 5

METHOD AND DEVICE FOR DETERMINING A BLOOD CONSTITUENT

CROSS REFERENCE TO RELATED APPLICATIONS

The present application claims priority to U.S. Provisional Application Ser. No. 61/565,525, filed on Dec. 1, 2011, and Application No. DE 10 2011 119 824.9, filed in the Federal Republic of Germany on Dec. 1, 2011, the contents of which are expressly incorporated herein in their entirety by reference thereto.

FIELD OF INVENTION

The present invention relates to a method and a device for determining the concentration of constituents of blood, in particular haemoglobin, haematocrit, glucose, creatinin and bilirubin, in a hose line of an extracorporeal blood circuit of an extracorporeal blood treatment apparatus. Furthermore, the present invention relates to an extracorporeal blood treatment apparatus with a device for determining the concentration of a blood constituent.

BACKGROUND INFORMATION

Various methods are known for determining the concentration of specific constituents of a patient's blood. Methods for measuring the concentration of blood constituents which require a blood sample to be taken are known in the prior art. Measuring methods are however also known in which the concentration of blood constituents in blood flowing through a hose line can be measured. These methods are used especially when the blood is flowing through the hose line of an extracorporeal blood circuit in an extracorporeal blood treatment.

In an extracorporeal blood treatment, particularly in a blood treatment with a haemodialysis machine, the monitoring of the concentration of haemoglobin in the patient's blood is important. Frequent measurements of the haemoglobin concentration enable the early detection of the therapeutic effect through a trend analysis and permit early adaptation of the therapeutic measures.

International Patent Publication No. WO 2008/000433 A1 describes a method and a device for determining the concentration of specific blood constituents in a blood-filled, essentially transparent hose line, in particular a hose line of an extracorporeal blood circuit of an extracorporeal blood treatment apparatus. The known method and the known device make it possible in particular to determine the haemoglobin concentration and the haematocrit.

During the measurement, the hose line is clamped between two parallel, plane contact surfaces, so that the hose is deformed at the sides lying opposite one another. The measurement of the haematocrit is based on the transmission or scattering of electromagnetic radiation of a specific wavelength in the blood. With an emitter, the electromagnetic radiation is coupled through the transparent hose line into the blood, whilst with a detector the scattered transmitted electromagnetic radiation is decoupled from the blood. The haematocrit is then determined from the analysis of the decoupled radiation. The concentrations of other blood constituents, for example, creatinin, bilirubin, glucose, etc., can however also be determined with the known scattered-light or transmission or reflection measurement.

The intensity of the decoupled light depends not only on the concentration of the blood constituents, but also on other factors. The concentration of the blood constituents cannot therefore be readily calculated from the analysis of the decoupled light.

German Application No. DE 10 2010 026 723.6 describes that, in the scattered-light or transmission or reflection measurement, a role is played by the properties of the hose line through which the light is coupled and decoupled. The hose line influences the optical measurement, since the hose partially absorbs and scatters the light. A compensation of the influence of the hose line on the determination of the haemoglobin concentration is therefore provided for.

A method for the quantitative determination of dissolved substances by the light scatter of a laser is described in European Patent Application No. EP 0 074 428. The described method permits the measurement of blood constituents, in particular glucose, in suitable parts of the body, e.g., the earlobe. It can be deduced from the publication that difficulties can in principle arise from the changing flow of blood through the earlobe during the measurement. European Patent Application No. EP 0 575 712 describes a spectrophotochemical blood analysis.

SUMMARY

The present invention provides a method with which a blood constituent in a hose line of an extracorporeal blood circuit can be determined with a high degree of accuracy. The present invention also makes available a device with which a blood constituent in a hose line of an extracorporeal blood circuit can be determined with a high degree of accuracy. The present invention also provides an extracorporeal blood treatment apparatus, in particular a haemodialysis apparatus, with a device for determining a blood constituent.

The method and device according to the present invention are based on the correction of the influence of the blood flow rate of the blood flowing through the hose line on the determination of the concentration of the blood constituent. The method and device according to the present invention require a basic calibration with a calibration blood flow rate.

For the determination of the concentration of the blood constituent, it is in principle irrelevant whether reflected, transmitted and/or scattered electromagnetic radiation is measured. The electromagnetic radiation, with which the measurement of the intensity of the electromagnetic radiation known to the person skilled in the art is carried out, preferably does not lie in the visible region of light, i.e., the electromagnetic radiation lies outside a wavelength of 380 nm to 780 nm.

A particularly preferred exemplary embodiment of the method and device according to the present invention is the determination of the haemoglobin concentration. In order to determine the haemoglobin concentration, the intensity of the electromagnetic radiation scattered sideways is preferably measured. Such a measurement procedure is described for example in International Patent Publication No. WO 2008/000433 A1.

It has been shown in tests that the influence of the blood flow rate on the determination of haemoglobin Hb cannot be overlooked in practice. It has been shown that the measurement error generally increases with an increasing deviation of the blood flow rate from the calibration blood flow rate. The influence of the blood flow rate on the measurement generally increases when the haemoglobin concentration rises.

The device according to the present invention comprises a device for coupling electromagnetic radiation through the hose line into the blood, a device for measuring the electromagnetic radiation decoupled from the blood through the hose line, and a computing and evaluation unit, which is constituted such that the concentration of the blood constituent is determined on the basis of a relationship describing the dependence of the concentration of the blood constituent on the intensity of the decoupled electromagnetic radiation.

The devices for coupling and decoupling the electromagnetic radiation can be constituted in different ways. Such devices are part of the prior art. The known devices for decoupling electromagnetic radiation supply a measurement signal, the amplitude whereof correlates with the intensity of the radiation.

The electromagnetic radiation can be coupled into the venous hose line or the arterial hose line or can be decoupled out of the venous or arterial hose line. The electromagnetic radiation is preferably coupled into the arterial hose line and decoupled out of the arterial hose line.

The computing and evaluation unit comprises a device for determining a correction factor for the influence of the blood flow rate on the determination of the concentration of the blood constituent. The concentration of the blood constituent is determined on the basis of the relationship describing the dependence of the concentration of the blood constituent on the intensity of the decoupled electromagnetic radiation, taking account of the correction factor.

The blood flow rate at which the blood flows through the hose line during the measurement can be a known blood flow rate which is preset by the medical personnel. In this case, the blood flow rate does not need to be explicitly determined. The blood flow rate can however also be measured during the blood treatment.

The determination of the correction factor can be carried out during the extracorporeal blood treatment or before or after the blood treatment. The basic principle of these exemplary embodiments is explained below.

In a first exemplary embodiment, a relationship describing the dependence of the correction factor on the blood flow rate is ascertained and stored in order to determine the correction factor before the extracorporeal blood treatment is carried out. During the extracorporeal blood treatment, the correction factor for the current blood flow rate at which the blood is flowing through the hose line is then calculated from the known relationship describing the dependence of the correction factor on the blood flow rate. The concentration of the blood constituent is then determined on the basis of the relationship describing the dependence of the concentration of the blood constituent on the intensity of the decoupled electromagnetic radiation, taking account of the calculated correction factor.

The correction by means of the correction factor can take place in several steps. At the start of the extracorporeal treatment, a first correction factor can be calculated for a preset blood flow rate and the blood constituent is determined taking account of the first correction factor, wherein a second correction factor can be calculated following a change in the blood flow rate during the extracorporeal blood treatment that is greater than a preset amount and the blood constituent can be determined taking account of the second correction factor. After the second correction, further corrections can take place during the blood treatment if the blood flow rate changes again.

It has been shown in tests that the relationship describing the dependence of the correction factor on the blood flow rate can be described with sufficient accuracy by a polynomial of the first degree.

An advantage of the first exemplary embodiment lies in the fact that the blood flow rate does not have to be changed in order to determine the correction factor during the blood treatment. The determination of the correction factor can therefore take place without intervention into the blood treatment. The measurement of the relevant quantities and the calculation of the relevant parameters can take place fully automatically by means of the device for determining the blood constituent.

An alternative exemplary embodiment provides for a determination of the correction factor during the blood treatment. This exemplary embodiment, however, requires a change in the blood flow rate during the blood treatment, albeit only a brief one. An advantage of this exemplary embodiment lies in the fact that the determination of a relationship describing the dependence of the correction factor on the blood flow rate is not required in the context of a basic calibration. The correction factor can be ascertained precisely during the blood treatment. Here too, a fundamental intervention by the medical personnel into the blood treatment is again unnecessary. The measurement of the relevant quantities and the calculation of the relevant parameters can again be carried out fully automatically.

In this alternative exemplary embodiment, the intensity of the decoupled electromagnetic radiation is first ascertained and stored for a calibration blood flow rate. The correction preferably takes place only in the presence of a significant deviation of the current blood flow rate from the calibration blood flow rate. The electromagnetic radiation decoupled from the blood through the hose line is measured both for the current blood flow rate as well as for the calibration blood flow rate. In order to measure the electromagnetic radiation at the calibration blood flow rate, the blood flow rate is adjusted to the calibration blood flow rate for a preset time interval, preferably only in the presence of a significant deviation of the current blood flow rate from the calibration blood flow rate. The correction factor is then calculated on the basis of the electromagnetic radiation measured for the current blood flow rate and the calibration blood flow rate.

An increase in the blood flow rate during the extracorporeal blood treatment may not be desirable for specific reasons. For example, the adjustment of a particularly high blood flow rate in patients with a problem with the blood access (shunt) can be critical. A further particularly preferred exemplary embodiment therefore provides for a safety test, which consists in calculating the amount of the difference between the current blood flow rate and the calibration blood flow rate, wherein the blood flow rate is adjusted to the calibration blood flow rate for a preset time interval only when the amount of the difference between the current blood flow rate and the calibration blood flow rate is less than a preset threshold value. This threshold value can be a value specific to the given patient or can be a fixedly preset value.

The deviation of the current blood flow rate from the calibration blood flow rate is preferably monitored continuously during the extracorporeal blood treatment, wherein the blood flow rate is adjusted to the calibration blood flow rate for a preset time interval and the correction factor is calculated only in the presence of a deviation of the current blood flow rate from the calibration blood flow rate that is greater than a preset amount, but preferably less than the preset threshold value.

During the preset time interval, the ultrafiltration rate at which fluid is withdrawn from the extracorporeal blood circuit is preferably set to zero, so that fluid is not withdrawn from the blood circuit during the measurement with the increased or reduced blood flow rate. The effect of this is that the concentration of the blood constituent before and after the adjustment of the blood flow rate remains the same. The adjustment of the ultrafiltration rate to zero is however not absolutely essential if the electromagnetic radiation is coupled into the arterial hose line and decoupled out of the arterial hose line. The ultrafiltration via the fistula recirculation can then exert only a relatively slight influence on the concentration of the blood constituent.

A further alternative exemplary embodiment requires a separation of the patient from the extracorporeal blood circuit and a short circuit of the arterial and venous hose line, in order to ascertain a relationship describing the dependence of the correction factor on the blood flow rate. With a short-circuited arterial and venous hose line, the electromagnetic radiation decoupled from the blood through the hose line is measured for different blood flow rates, and the correction factor is determined on the basis of the electromagnetic radiation measured for the different blood flow rates.

In a preferred exemplary embodiment, a distinction is made between the case where the current blood flow rate is greater or less than a calibration blood flow rate. A first relationship describing the dependence of the correction factor on the blood flow rate is determined for a blood flow rate which is greater than the preset calibration blood flow rate and a second relationship describing the dependence of the correction factor on the blood flow rate is determined for a blood flow rate which is less than the preset calibration blood flow rate. Both correction factors can be stored in a memory of the device for determining the blood constituent and can be used for the correction at the current blood flow rate, which may be greater or less than the calibration blood flow rate.

The aforementioned exemplary embodiments can be used as alternatives or in combination for the determination of a blood constituent. All the methods can therefore be implemented in the device for determining the blood constituent.

In principle, preference is given to the second method. The second method can always be used when the blood flow rate adjusted by the user is greater than the calibration blood flow rate. In this case, the blood flow rate does not need to be increased, but only reduced, which is uncritical for the patient. If, however, the adjusted blood flow rate is less than the calibration blood flow rate and an increase in the blood flow is to be ruled out for safety reasons, use may be made of the first method. It is for example also possible to use the first method solely for a one-off initial correction and then to carry out the further adaptation with the second method.

Various exemplary embodiments of the present invention are described in greater detail below with reference to the accompanying drawings.

DETAILED DESCRIPTION

Figure 1:
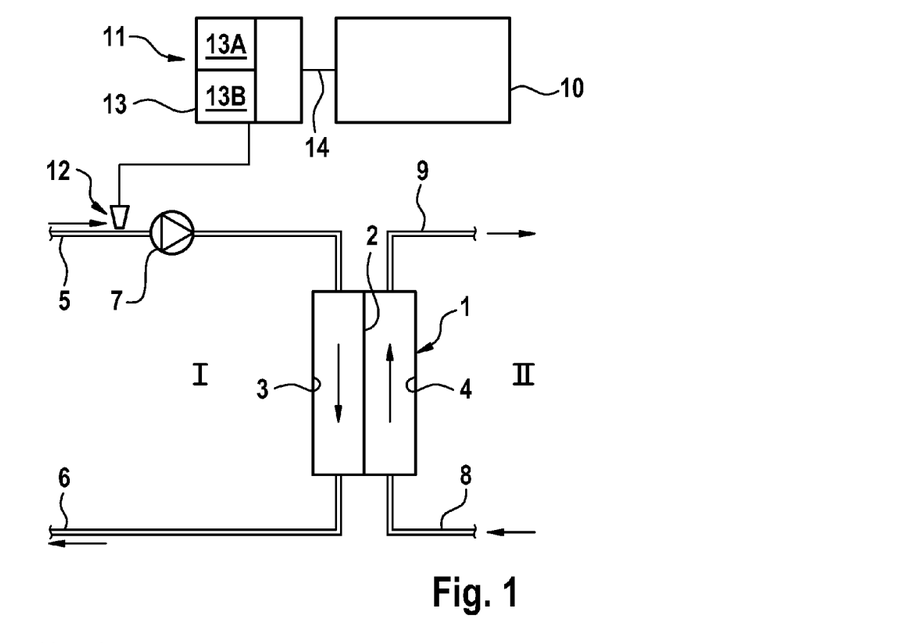
FIG. 1 shows an apparatus for extracorporeal blood treatment together with a device for determining the concentration of a blood constituent, in particular the haemoglobin concentration, in a very simplified diagrammatic representation.

FIG. 1 shows only the components of an apparatus for extracorporeal blood treatment that are relevant to the present invention, in a very simplified diagrammatic representation. The extracorporeal blood treatment apparatus, for example a dialysis apparatus, comprises a dialyser or filter 1, which is divided by a semipermeable membrane 2 into a blood chamber 3 and a dialysing fluid chamber 4. An arterial blood line 5 leads from the patient to the blood chamber, whilst a venous blood line 6 leads away from the blood chamber and to the patient.

A blood pump 7 disposed in arterial blood line 5 conveys the blood in extracorporeal circuit I.

Dialysing fluid system II of the dialysis apparatus is represented only in outline. It comprises a dialysing fluid supply line 8 leading to dialysing fluid chamber 4 and a dialysing fluid discharge line 9 leading away from dialysing fluid chamber 4.

Arterial and venous blood lines 5, 6 are essentially hose lines which are at least partially permeable to electromagnetic radiation, in particular to electromagnetic radiation having a wavelength that does not lie in the visible region from 380 nm to 780 nm and particularly preferably lies at a wavelength of 805 nm.

Furthermore, the blood treatment apparatus comprises a central control and computing unit 10, with which all the control and computing operations required for the control of the blood treatment apparatus are carried out, e.g., with which the individual components, for example blood pump 7, are controlled. Control and computing unit 10 also permits the adjustment of a specific ultrafiltration rate, at which fluid is withdrawn from the patient via membrane 2 of dialyser 1 during the blood treatment.

Device 11 according to the present invention for determining the concentration of specific blood constituents in the patient's blood can be a component of the extracorporeal blood treatment apparatus or form a separate unit. If device 11 according to the present invention is a component of the blood treatment apparatus, it can make use of components which are in any case present in the blood treatment apparatus. In particular, device 11 according to the present invention can make use of control and computing unit 10.

Device 11 for determining the concentration of a blood constituent comprises devices 12, represented only in outline in FIG. 1, for coupling and decoupling electromagnetic radiation, said devices being a component of a measuring arrangement. In the present exemplary embodiment, moreover, device 11 comprises its own computing and evaluation unit 13, which is connected via a data line 14 to central control and computing unit 10 of the blood treatment apparatus. It is however also possible for computing and evaluation unit 13 to be a component of control and computing unit 10 of the blood treatment apparatus.

Figure 2:
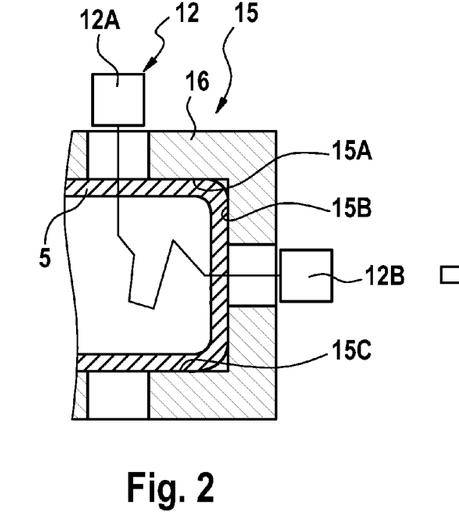
FIG. 2 shows the devices for the coupling and decoupling of electromagnetic radiation in a very simplified diagrammatic representation.

FIG. 2 shows, in a very simplified diagrammatic representation, a cross-section through measuring arrangement 15 with devices 12 for the coupling (12A) and decoupling (12B) of electromagnetic radiation. Such a measuring arrangement 15 for the determination of the concentration of a blood constituent, for example haemoglobin, is known to the person skilled in the art. Measuring arrangement 15 comprises a device 16 for clamping hose line 5. Hose line 5 is clamped in device 16 in such a way that electromagnetic radiation can enter into and exit out of the hose line at planar boundary faces 15A, 15B, 15C. The known measuring arrangements permit the measurement of electromagnetic radiation reflected, transmitted or scattered in the blood. The electromagnetic radiation is emitted by one or more light emitters 12A, for example LEDs, and is received by one or more light detectors, for example photodiodes. Measuring arrangements with four light emitters and eight light detectors are known, in order to be able to detect the optical reflection/back-scattering (BS), transmission/forward-scattering (FS) and/or side-scattering (SS). The output signals of the individual light detectors 12B can be evaluated individually or in combination in order to determine the blood constituent.

Figure 2A:
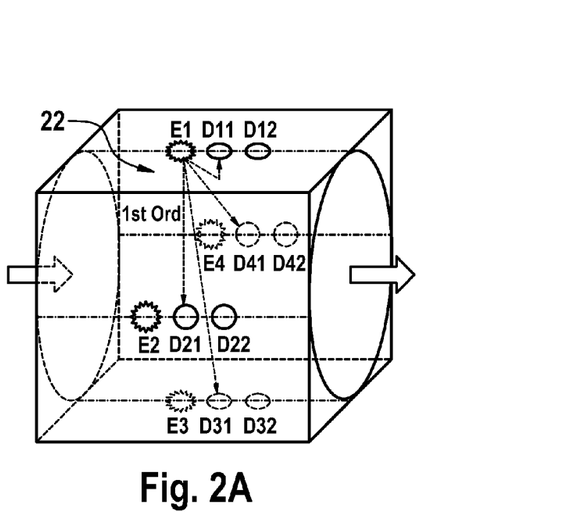
FIG. 2A shows a measuring arrangement with four light emitters and eight light detectors in a diagrammatic representation.

FIG. 2A shows in a diagrammatic representation a measuring arrangement 22 with four light emitters E1, E2, E3, E4 and eight light detectors D11, D21, D31, D41, D12, D22, D32, D42, which together form a measuring device for a transmission measurement, a scattered-light measurement and a reflection measurement. It can be seen from FIG. 2A that the light emitters and light detectors are disposed offset with respect to one another. This measuring device is described in International Patent Publication Nos. WO 2004/057313 A1 and WO 2010/115621 A3, which are expressly incorporated herein by reference thereto.

In the following, it is assumed that only the side-scattering (SS) is detected, the SS output signal of the light detector or the light detectors being evaluated.

The concentration of haemoglobin (Hb) as a blood constituent can be measured as follows:

$$Hb = a \cdot S(Q_{bk})^{-b} \qquad \text{(equation 1)}$$

wherein a and b are constants, which are ascertained in a basic calibration of measuring arrangement 15 carried out in the factory in the presence of a calibration blood flow rate $Q_{bk}$. $S(Q_{bk})$ is the measurement signal correlating with the side-scattering in the calibration of the measuring arrangement carried out in the factory.

The inventors have ascertained that the blood flow rate exerts an influence on the accuracy of the determination of the blood constituent, for example haemoglobin, that is not negligible in practice. The present invention therefore makes provision to correct the influence of the blood flow rate on the determination of the blood constituent.

Computing and evaluation unit 13 of device 11 according to present the invention for determining the concentration of a blood constituent, in particular haemoglobin (Hb), comprises a device 13A for determining a correction factor k.

The haemoglobin concentration is calculated in computing and evaluation unit 13 taking account of correction factor k according to the following equation.

$$Hb = a \cdot [k \cdot S(Q_b)]^{-b} \qquad \text{(equation 2)}$$

The calculation of correction factor k in evaluation and computing unit 13 is described in detail below.

A first exemplary embodiment provides for the determination of a function describing the dependence of correction factor k on the blood flow rate as part of a basic calibration carried out in the factory, which in the present exemplary embodiment is a polynomial of the first degree.

Computing and evaluation unit 13 comprises a memory 13B, in which the polynomial ascertained as part of the calibration carried out in the factory is stored, so that correction factor k can be calculated continuously by computing and evaluation unit 13 as a function of the current blood flow rate during the blood treatment.

As part of the basic calibration carried out in the factory, signal $S_n(Q_{bk})$ correlating with the side-scattering is first measured at calibration blood flow rate $Q_{bk}$ using devices 12 for coupling and decoupling the electromagnetic radiation of measuring arrangement 15. Constants a and b of equation (1) are then ascertained for calibration blood flow rate $Q_{bk}$. All the values are stored in memory 13B.

A number of measurements for different blood flow rates $Q_{bk}(i)$ are then carried out with a fixed value for the haemoglobin concentration, which typically lies at 11 g/dl. Measured signals $S_n(Q_b(i))$ are standardised to signal value $S_n(Q_{bk})$, which has been measured at calibration blood flow rate $Q_{bk}$. The following results:

$$R_n(i) = S_n(Q_b(i))/S_n(Q_{bk}) \qquad \text{equation (3)}$$

With a linear regression of obtained data pairs $R_n(i)$–$Q_b(i)$, a typical correction curve is calculated, which is described by the following linear equation:

$$R = m \cdot Q_b + n \qquad \text{equation (4)}$$

wherein m is the gradient and n is the offset of the curves (R [%] and $Q_b$ [ml/min]).

Figure 3:
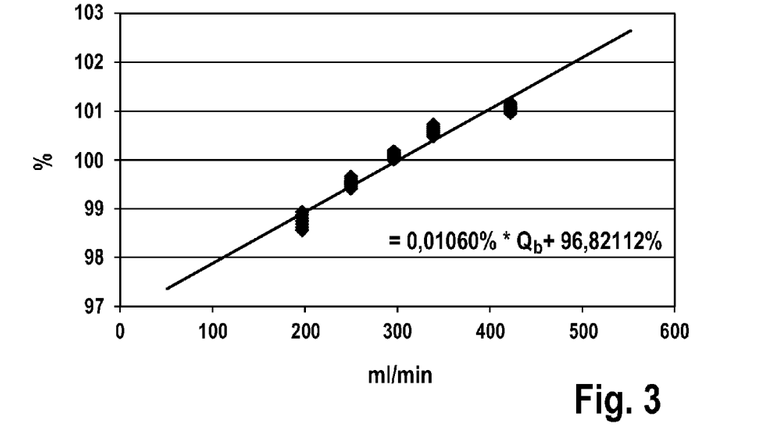
FIG. 3 shows the correction curve ascertained by a linear regression for the correction of the measured values.

FIG. 3 shows the correction curve ascertained from the data pairs. Equation (4) and the values for m and n are stored in memory 13B.

$$R = 0.0106 \cdot Q_b + 96.8211 \qquad \text{equation (5)}$$

During the blood treatment, signal $S(Q_b)$ is evaluated by computing and evaluation unit 13 at the current blood flow rate, which is set by the user. Computing and evaluation unit 13 also detects current blood flow rate $Q_b$. Computing and evaluation unit 13 calculates the amount of the difference between current blood flow rate $Q_b$ and calibration blood flow rate $Q_{bk}$. If the amount of the difference between current blood flow rate $Q_b$ and calibration blood flow rate $Q_{bk}$ is greater than a preset threshold value, a correction factor is calculated, with which a correction of signal $S(Q_b)$ measured at the current blood flow rate is carried out. The threshold value is set in such a way that a correction takes place only in the presence of a significant change of the blood flow rate, for example in the presence of a change of ≥30 ml.

If current blood flow rate $Q_b$ deviates by a significant amount from calibration blood flow rate $Q_{bk}$, computing and evaluation unit 13 corrects the measured value by means of the stored correction curves. The correction factor is calculated by computing and evaluation unit 13 with the stored values for m and n according to the following equation:

$$k = \frac{100\%}{m \cdot Q_b + n} \qquad \text{equation (6)}$$

Equation (6) can be derived as follows. With the correction curves (equations (4) and (5)), signal $S(Q_b)$ measured at current blood flow rate $Q_b$ is standardised to calibration blood flow rate $Q_{bk}$.

$$S(Q_{bk}) = \frac{100\%}{R} \cdot S(Q_b) \qquad \text{equation (7)}$$

The following results from equations (4) and (7)

$$S(Q_{bk}) = \frac{100\%}{m \cdot Q_b + n} \cdot S(Q_b) \qquad \text{equation (8)}$$

$$S(Q_{bk}) = k \cdot S(Q_b) \qquad \text{equation (9)}$$

Equation (6) results from equations (8) and (9).

After ascertainment of correction factor k, computing and evaluation unit 13 calculates the haemoglobin concentration for current blood flow rate $Q_b$, which deviates from calibration blood flow rate $Q_{bk}$, according to equation (2).

Following an initial correction, the calculation of a new correction factor and a subsequent correction can be carried out at any time when the current blood flow rate changes.

A second exemplary embodiment is described below, wherein the correction factor is calculated during the blood treatment, without a function describing the dependence of the correction factor on the blood flow rate being determined beforehand.

During the blood treatment, signal $S(Q_b)$ is again evaluated by computing and evaluation unit 13 at the current blood flow rate which has been set by the user. Computing and evaluation unit 13 again detects current blood flow rate $Q_b$ and calculates the amount of the difference between current blood flow rate $Q_b$ and calibration blood flow rate $Q_{bk}$. If the amount of the difference between current blood flow rate $Q_b$ and calibration blood flow rate $Q_{bk}$ is greater than a preset threshold value, computing and evaluation unit 13 generates a control signal which is received by central control and computing unit 10 of the blood treatment apparatus. Control and computing unit 10 then sets an ultrafiltration rate of zero for a preset time interval and during this time interval sets a blood flow rate which corresponds to calibration blood flow rate $Q_{bk}$.

Before or after the preset time interval, signal $S(Q_{b1})$ is measured for current blood flow rate $Q_{b1}$, whilst signal $S(Q_{bk})$ is measured for calibration blood flow rate $Q_{bk}$ in the time interval. After expiry of the time interval, the original ultrafiltration and blood-flow rate is again set.

Since, on account of the interruption of the ultrafiltration, the haemoglobin concentration remains the same before and after the adjustment of the blood flow rate, the correction factor is calculated as follows:

$$a \cdot S(Q_{bk})^{-b} = a \cdot [k_1 \cdot S(Q_{b1})]^{-b}$$

$$k_1 = \frac{S(Q_{bk})}{S(Q_{b1})}$$

Computing and evaluation unit 13 calculates correction factor k from measured signal values $S(Q_{bk})$ and $S(Q_{b1})$ according to equation (10) and, with the calculated correction factor, the haemoglobin concentration for current blood flow rate $Q_{b1}$ according to the following equation:

$$Hb = a \cdot [k \cdot S(Q_{b1})]^{-b} \qquad \text{equation (11)}$$

If, in the course of the blood treatment, computing and evaluation unit 13 ascertains a further significant change in the blood flow rate that is greater than the preset threshold value, the computing and evaluation unit adapts the correction factor to changed current blood flow rate $Q_{b2}$. This adaptation takes place continuously in iterative steps throughout the blood treatment.

For blood flow rate $Q_{b2}$, the following results:

$$a \cdot S(Q_{b1})^{-b} = a \cdot [k_2 \cdot S(Q_{b2})]^{-b} \qquad \text{equation (12)}$$

$$k_2 = \frac{S(Q_{b1})}{S(Q_{b2})}$$

$$S(Q_{b1}) = k_2 \cdot S(Q_{b2}) \qquad \text{equation (13)}$$

$$S(Q_{bk}) = k_1 k_2 \cdot S(Q_{b2}) \qquad \text{equation (14)}$$

$$Hb = a \cdot [k_1 k_2 \cdot S(Q_{b2})]^{-b} \qquad \text{equation (15)}$$

Computing and evaluation unit 13 then calculates correction factor $k_2$ from measured signal values $S(Q_{b1})$ and $S(Q_{b2})$ according to equation (12) for the subsequent correction step. For current blood flow rate $Q_{b2}$, computing and evaluation unit 13 calculates haemoglobin concentration Hb from correction factor $k_1$ ascertained in the preceding correction step and correction factor $k_2$ for the subsequent correction step according to equation (15).

In order to increase the safety for the patient, computing and evaluation unit 13 also provides a safety routine. Computing and evaluation unit 13 calculates the difference between calibration blood flow rate $Q_{bk}$ and current blood flow rate $Q_b$. If calibration blood flow rate $Q_{bk}$ is less than current blood flow rate $Q_b$, i.e., the difference between calibration blood flow rate $Q_{bk}$ and current blood flow rate $Q_b$ is a negative value, there is no safety risk for the patient, since blood flow rate $Q_b$ is not increased, but rather reduced in the preset time interval for the measurement, which is uncritical even in patients with shunt problems.

If, on the other hand, computing and evaluation unit 13 ascertains that calibration blood flow rate $Q_{bk}$ is greater than current blood flow rate $Q_b$, i.e., the difference between calibration blood flow rate $Q_{bk}$ and current blood flow rate $Q_b$ is positive, a risk may exist for patients with shunt problems. In this case, the increase in the blood flow rate for the measurement can be prevented in a first exemplary embodiment. Computing and evaluation unit 13 then does not generate a control signal. An alternative exemplary embodiment makes provision to generate a control signal only when the difference between calibration blood flow rate $Q_{bk}$ and current blood flow rate $Q_b$ is less than a preset threshold value. This threshold value should be dimensioned such that a risk to a patient with shunt problems due to a brief increase in the blood flow rate is reliably ruled out.

A further exemplary embodiment is described below, wherein the correction factor is determined with a short circuit of the arterial and venous blood line.

Computing and evaluation unit 13 generates, preferably at the start of the blood treatment, a control signal which is received by control and computing unit 10 of the blood treatment apparatus. The control signal can however also be generated during the blood treatment, for example in the middle or at the end. After receiving this control signal, control and computing unit 10 initiates the steps required to ascertain the correction factor. A short circuit of the arterial and venous hose line is first produced, wherein the patient is separated from the hose system. The step can in principle also take place manually, but preferably the arterial and venous hose lines are connected via a bypass which is automatically switched on. For this purpose, valves or suchlike can be provided in the hose line system, which are opened or closed by control and computing unit 10.

While the patient's blood is circulating in the extracorporeal blood circuit, signal $S(Q_b)$ is measured for different blood flow rates $Q_b$, for example $S(Q_{bk})$, $S(Q_{b1})$ and $S(Q_{b2})$.

Computing and evaluation unit 13 calculates the difference between calibration blood flow rate $Q_{bk}$ and current blood flow rate $Q_b$. If computing and evaluation unit 13 ascertains that calibration blood flow rate $Q_{bk}$ is greater than current blood flow rate $Q_b$, i.e., the difference between calibration blood flow rate $Q_{bk}$ and current blood flow rate $Q_b$ is a positive value, computing and evaluation unit 13 calculates correction factor K_ according to the following equation:

$$k_- = \frac{S(Q_{bk})}{S(Q_{b1})} \cdot \frac{Q_{bk} - Q_b}{Q_{bk} - Q_{b1}} \quad \text{equation (16)}$$

for $$Q_b < Q_{bk}$$

If, on the other hand, calibration blood flow rate $Q_{bk}$ is less than current blood flow rate $Q_b$, i.e., the difference between calibration blood flow rate $Q_{bk}$ and current blood flow rate $Q_b$ is negative, computing and evaluation unit 13 calculates correction factor $K_+$ according to the following equation:

$$k_+ = \frac{S(Q_{bk})}{S(Q_{b1})} \cdot \frac{Q_b - Q_{bk}}{Q_{b2} - Q_{bk}} \quad \text{equation (17)}$$

for $$Q_b > Q_{bk}$$

Correction factors $K_-$ and $K_+$ are stored in memory 13B. During the blood treatment, computing and evaluation unit 13 calculates haemoglobin concentration Hb in the presence of a significant positive or negative deviation of current blood flow rate $Q_b$ from calibration blood flow rate $Q_{bk}$ with respective correction factor $K_-$ or $K_+$ according to the following equation:

$$Hb = a \cdot [k_\pm \cdot S(Q_{b1})]^{-b} \quad \text{(equation 18)}$$

In a test with cattle blood using the measuring arrangement described above, the haemoglobin concentration [g/dl] in the blood was measured for different blood flow rates $Q_b$ from 100 to 500 ml/min at five different haemoglobin working points (7.04, 8.03, 10.43, 12.83 and 15.8 g/dl).

Figure 4:
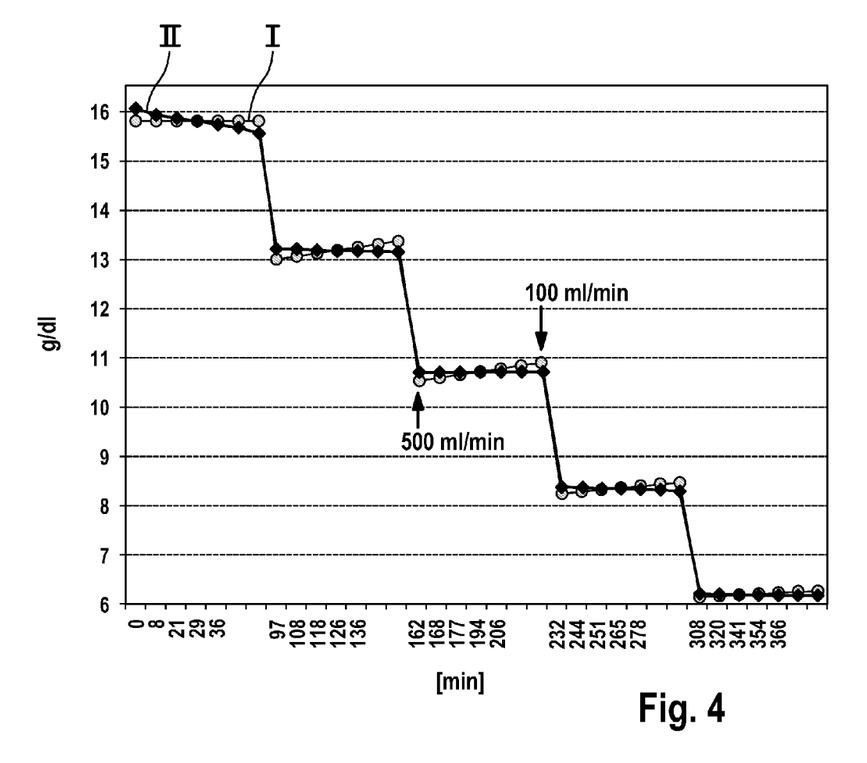
FIG. 4 shows a representation to illustrate the measured haemoglobin concentration before and after the correction of the measured values.
Figure 5:
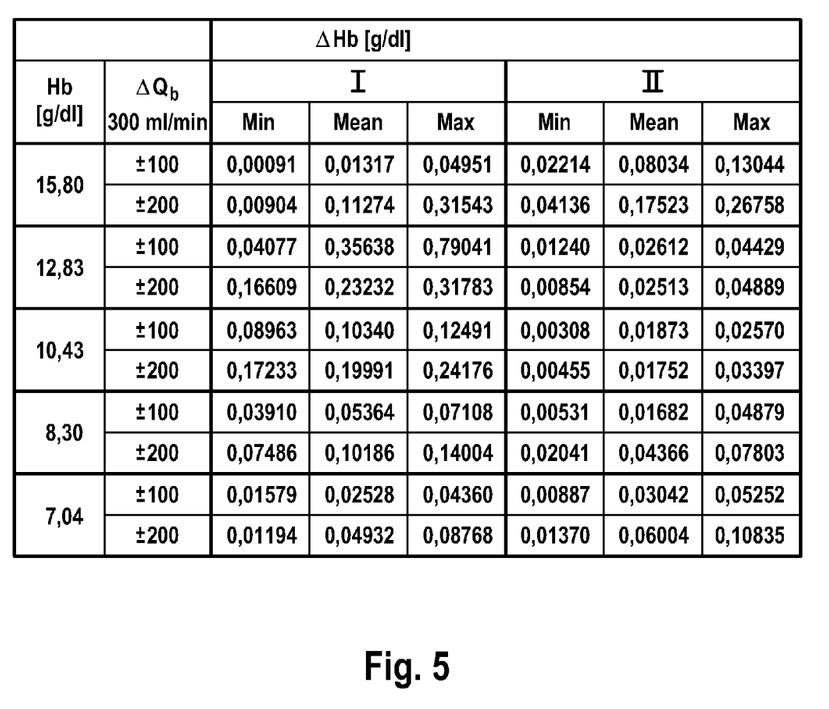
FIG. 5 shows a table with the measurement results before and after the correction of the measured values.

FIG. 4 shows the course of the measured haemoglobin concentration [g/dl] before the correction (I) of the measured values and after the correction (II) with the method according to the present invention as a function of blood flow rate $Q_b$ at the different haemoglobin working points (7.04, 8.03, 10.43, 12.83 and 15.8 g/dl). The measurement results are summarised in a table (FIG. 5). The table shows the minimum (Min), maximum (Max) or mean (Mean) measurement error ΔHb [g/dl] before the correction (I) and after the correction (II) for the different haemoglobin working points (7.04, 8.03, 10.43, 12.83 and 15.8 g/dl), wherein the blood flow rate has been increased and reduced proceeding from 300 ml/min in each case by +/−100 ml and +/−200 ml, respectively.

It appears that measurement error ΔHb [g/dl] is systematic, its amount as a rule increasing with the increase in the $Q_b$-deviation $\Delta Q_b = |Q_b - 300|$. he influence of $Q_b$ on haemoglobin concentration Hb increases as a rule with the increase in the haemoglobin concentration.

When $Q_{bk}$=300 ml/min and Hb=10.43 g/dl, the $Q_b$-related Hb measurement error amounts to ±0.10 g/dl with $\Delta Q_b$=±100 ml/min and ±0.20 g/dl with $\Delta Q_b$=±200 ml/min.

What is claimed is:

1. A method for determining a concentration of a blood constituent during an extracorporeal blood treatment performed by an extracorporeal blood treatment apparatus including a central control and computing unit that performs control and computing operations of the extracorporeal blood treatment apparatus, wherein blood flows through an arterial hose line into a blood chamber and via a venous hose line out of the blood chamber of a dialyser divided by a semipermeable membrane into the blood chamber and a dialysing fluid chamber, the method comprising:
    calibrating, prior to use in the extracorporeal blood treatment, a measuring arrangement using a calibration blood flow rate;
    storing the calibration blood flow rate in a memory of a computing and evaluation unit;
    determining, via the central control and computing unit, a current blood flow rate;
    storing the current blood flow rate in the memory of the computing and evaluation unit;
    setting a preset threshold value for the difference between the current blood flow rate and the calibration blood flow rate;
    storing the preset threshold value in the memory of the computing and evaluation unit;
    coupling, via an emitter device of the measuring arrangement, electromagnetic radiation through the arterial hose line or the venous hose line into the blood;
    measuring, via a detector of the measuring arrangement, the electromagnetic radiation decoupled through the arterial hose line or the venous hose line from the blood;
    ascertaining, via the computing and evaluation unit, a correction factor to correct for an influence of the blood flow rate on a determination of the concentration of the blood constituent wherein the correction factor is ascertained only if a deviation between the current blood flow rate and the calibration blood flow rate is greater than the preset threshold value as determined by the computing and evaluation unit;
    determining, via a determining device, the concentration of the blood constituent based on (a) a relationship describing a dependence of the concentration of the blood constituent on a measured intensity of the decoupled electromagnetic radiation, and (b) the correction factor; and
    transmitting the concentration of the blood constituent from the determining device to the central control and computing unit of the extracorporeal blood treatment apparatus.

2. The method according to claim 1, wherein the relationship describing the dependence of the concentration of the blood constituent on the measured intensity of the decoupled electromagnetic radiation is described by the following equation:

$$Hb = a \cdot S(Q_{bk})^{-b}$$

wherein a and b are constants and $S(Q_{bk})$ is a measurement signal correlating with the measured intensity of the decoupled electromagnetic radiation.

3. The method according to claim 1, wherein, if the deviation between the current blood flow rate and the calibration blood flow rate is greater than the preset threshold value as determined by the computing and evaluation unit, in order to take account of the blood flow, the relationship describing the dependence of the concentration of the blood constituent on the measured intensity of the decoupled electromagnetic radiation is corrected as follows:

$$Hb = a \cdot [k \cdot S(Q_b)]^{-b}$$

wherein $S(Q_b)$ is the measurement signal correlating with the measured intensity of the decoupled electromagnetic radiation and k is the correction factor.

4. The method according to claim 1, further comprising, before the extracorporeal blood treatment is carried out:

ascertaining a relationship describing dependence of the correction factor on the blood flow rate; and storing the relationship describing the dependence of the correction factor on the blood flow rate;

wherein ascertaining the correction factor for the blood flow rate during the extracorporeal blood treatment comprises calculating the correction factor from the relationship describing the dependence of the correction factor on the blood flow rate.

5. The method according to claim 4, further comprising, at a start of the extracorporeal blood treatment:

determining that a deviation between the preset blood flow rate and the calibration blood flow rate is greater than the preset threshold value as determined by the computing and evaluation unit and calculating a first correction factor for a preset blood flow rate;

determining the concentration of the blood constituent taking account of the first correction factor;

calculating a second correction factor following a change in the blood flow rate during the extracorporeal blood treatment that is greater than the preset threshold value; and determining the concentration of the blood constituent taking account of the second correction factor.

6. The method according to claim 4, wherein the relationship describing the dependence of the correction factor on the blood flow rate is a polynomial of the first degree.

7. The method according to claim 1, wherein ascertaining the correction factor comprises:

ascertaining a measured intensity of the decoupled electromagnetic radiation for the calibration blood flow rate;

adjusting the blood flow rate to the calibration blood flow rate for a preset time interval; and measuring the electromagnetic radiation decoupled through the one of the arterial hose line or the venous hose line from the blood for the current blood flow rate and for the calibration blood flow rate;

wherein the correction factor is calculated based on the electromagnetic radiation measured for the current blood flow rate and the calibration blood flow rate.

8. The method according to claim 7, wherein a correction factor (k) is calculated according to the following equation:

$$k = \frac{S(Q_{bk})}{S(Q_{b1})}$$

wherein $S(Q_{b1})$ is a measurement signal correlating with the measured intensity of the decoupled electromagnetic radiation for current blood flow rate $Q_{b1}$ and $S(Q_{bk})$ is a measurement signal correlating with the measured intensity of the decoupled electromagnetic radiation for calibration blood flow rate $Q_{bk}$.

9. The method according to claim 7, further comprising:

calculating a difference between the current blood flow rate and the calibration blood flow rate;

determining that the current blood flow rate is less than the calibration blood flow rate;

determining that the deviation between the current blood flow rate, and the calibration blood flow rate as determined by the computing and evaluation unit, is greater than the preset threshold value and less than a second preset threshold value; and adjusting the blood flow rate to the calibration blood flow rate for a preset time interval.

10. The method according to claim 7, further comprising:

setting an ultrafiltration rate at which fluid is withdrawn from the extracorporeal blood circuit during the preset time interval to zero.

11. The method according to claim 1, wherein ascertaining the correction factor comprises:

measuring the electromagnetic radiation decoupled through the one of the arterial hose line or the venous hose line from the blood for different blood flow rates with a short-circuited arterial and venous hose line; and determining a relationship describing dependence of the correction factor on the blood flow rate based on the electromagnetic radiation measured for the different blood flow rates.

12. The method according to claim 11, wherein ascertaining the correction factor further comprises:

ascertaining an intensity of the decoupled electromagnetic radiation for the calibration blood flow rate;

determining a first relationship describing the dependence of the correction factor on the blood flow rate for a blood flow rate which is greater than the calibration blood flow rate; and determining a second relationship describing the dependence of the correction factor on the blood flow rate for a blood flow rate which is less than the calibration blood flow rate.

13. The method according to claim 12, wherein the first relationship describing the dependence of the correction factor on the blood flow rate is described by the following equation:

$$k_+ = \frac{S(Q_{bk})}{S(Q_{b1})} \cdot \frac{Q_b - Q_{bk}}{Q_{b2} - Q_{bk}}$$

for $$Q_b < Q_{bk}.$$

14. The method according to claim 12, wherein the second relationship describing the dependence of the correction factor on the blood flow rate is described by the following equation:

$$k_- = \frac{S(Q_{bk})}{S(Q_{b1})} \cdot \frac{Q_{bk} - Q_b}{Q_{bk} - Q_{b1}}$$

for $$Q_b < Q_{bk}.$$

15. The method according to claim 1, wherein the blood constituent is haemoglobin.

16. A determining device for determining a concentration of a blood constituent in a hose line of an extracorporeal blood treatment apparatus, the apparatus including a central control and computing unit to perform control and computing operations of the extracorporeal blood treatment apparatus, wherein blood flows through an arterial hose line into a blood chamber and via a venous hose line out of the blood chamber of a dialyser divided by a semipermeable membrane into the blood chamber and a dialysing fluid chamber, the determining device comprising:

a measuring arrangement, including a device configured to couple electromagnetic radiation through the arterial hose line or the venous hose line into the blood and a device configured to measure the electromagnetic radiation decoupled through the arterial hose line or the venous hose line from the blood; and a computing and evaluation unit, including a memory, configured to determine a correction factor to correct for an influence of a current blood flow rate on a determination of the concentration of the blood constituent;

wherein the measuring arrangement is calibrated prior to use in extracorporeal blood treatment, using a calibration blood flow rate, the calibration blood flow rate being stored in the memory of the computing and evaluation unit;

wherein the current blood flow rate is set by the central control and computing unit, the current blood flow rate being stored in the memory of the computing and evaluation unit;

wherein a preset threshold value for the difference between the current blood flow rate and the calibration blood flow rate is stored in the memory of the computing and evaluation unit;

wherein the computing and evaluation unit is configured to determine the correction factor only when a deviation between the current blood flow rate and the calibration blood flow rate is greater than the preset threshold value;

wherein the concentration of the blood constituent is determined based on (a) a relationship describing a dependence of the concentration of the blood constituent on a measured intensity of the decoupled electromagnetic radiation, and (b) the correction factor; and wherein the concentration of the blood constituent is transmitted from the determining device to the central control and computing unit of the extracorporeal blood treatment apparatus.

17. The device according to claim 16, wherein the relationship describing the dependence of the concentration of the blood constituent on the measured intensity of the decoupled electromagnetic radiation is described by the following equation:

$$Hb = a \cdot S(Q_{bk})^{-b}$$

wherein a and b are constants and $S(Q_b)$ is a measurement signal correlating with the measured intensity of the decoupled electromagnetic radiation.

18. The device according to claim 16, the computing and evaluation unit is configured to determine that the deviation between the current blood flow rate and the calibration blood flow rate is greater than the preset threshold value, and, in order to take account of the blood flow, the relationship describing the dependence of the concentration of the blood constituent on the measured intensity of the decoupled electromagnetic radiation is corrected as follows:

$$Hb = a \cdot [k \cdot S(Q_b)]^{-b}$$

wherein $S(Q_b)$ is a measurement signal correlating with the measured intensity of the decoupled electromagnetic radiation and k is the correction factor.

19. The device according to claim 16, wherein a relationship describing dependence of the correction factor on the blood flow rate is stored in the memory of the computing and evaluation unit, and the computing and evaluation unit is configured such that the correction factor to correct for the blood flow rate is calculated during the extracorporeal blood treatment from the relationship describing the dependence of the correction factor on the blood flow rate.

20. The device according to claim 19, wherein the computing and evaluation unit is configured such that: (a) at a start of the extracorporeal blood treatment, a first correction factor is calculated for a preset blood flow rate; (b) the concentration of the blood constituent is determined taking account of the first correction factor only if the deviation between the preset blood flow rate and the calibration blood flow rate is greater than the preset threshold value as determined by the computing and evaluation unit; (c) a second correction factor is calculated following a change in the blood flow rate during the extracorporeal blood treatment, which is greater than the preset threshold value; and (d) the concentration of the blood constituent is determined taking account of the second correction factor.

21. The device according to claim 19, wherein the relationship describing the dependence of the correction factor on the blood flow rate is a polynomial of the first degree.

22. The device according to claim 16, wherein a measured intensity of the decoupled electromagnetic radiation for the calibration blood flow rate is stored in the memory of the computing and evaluation unit, and the computing and evaluation unit is configured such that the electromagnetic radiation decoupled through the one of the arterial hose line or the venous hose line from the blood is measured for the current blood flow rate and for the calibration blood flow rate if the deviation of the current blood flow rate from the calibration blood flow rate is greater than the preset threshold value, wherein the correction factor is determined based on the electromagnetic radiation measured for the current blood flow rate and the calibration blood flow rate.

23. The device according to claim 22, wherein the correction factor (k) is determined according to the following equation:

$$k = \frac{S(Q_{bk})}{S(Q_{b1})}$$

wherein $S(Q_{b1})$ is a measurement signal correlating with the measured intensity of the decoupled electromagnetic radiation for current blood flow rate $Q_{b1}$, and $S(Q_{bk})$ is a measurement signal correlating with the measured intensity of the decoupled electromagnetic radiation for calibration blood flow rate $Q_{bk}$.

24. The device according to claim 22, wherein the computing and evaluation unit is configured such that, if the current blood flow rate is less than the calibration blood flow rate, a control signal is generated for the blood treatment apparatus for adjusting the blood flow rate for a preset time interval to the calibration blood flow rate only when the deviation between the current blood flow rate and the calibration blood flow rate is greater than the preset threshold value and less than a second preset threshold value as determined by the computing and evaluation unit.

25. The device according to claim 24, wherein the computing and evaluation unit is configured such that, if the control signal is generated to adjust the blood flow rate for a preset time interval to the calibration blood flow rate, then a control signal is generated for the blood treatment apparatus for adjusting an ultrafiltration rate, at which fluid is withdrawn from the extracorporeal blood circuit during the preset time interval, to zero.

26. The device according to claim 16, wherein the device in configured so that if the correction factor is to be determined, then electromagnetic radiation decoupled through the one of the arterial hose line or the venous hose line from the blood is measured for different blood flow rates with a short-circuited arterial and venous hose line and is stored in the memory of the computing and evaluation unit, and the computing and evaluation unit is configured such that a relationship describing dependence of the correction factor on the blood flow rate is determined based on the electromagnetic radiation measured for the different blood flow rates.

27. The device according to claim 26, wherein the computing and evaluation unit is configured such that, if the correction factor is to be determined, an intensity of the decoupled electromagnetic radiation is ascertained for the calibration blood flow rate, wherein a first relationship describing the dependence of the correction factor on the blood flow rate is determined for a blood flow rate which is greater than the calibration blood flow rate and a second relationship describing the dependence of the correction factor on the blood flow rate is determined for a blood flow rate which is less than the calibration blood flow rate.

28. The device according to claim 27, wherein the first relationship describing the dependence of the correction factor on the blood flow rate is described by the following equation:

$$k_+ = \frac{S(Q_{bk})}{S(Q_{b1})} \cdot \frac{Q_b - Q_{bk}}{Q_{b2} - Q_{bk}}$$

for $$Q_b > Q_{bk}.$$

29. The device according to claim 27, wherein the second relationship describing the dependence of the correction factor on the blood flow rate is described by the following equation:

$$k_- = \frac{S(Q_{bk})}{S(Q_{b1})} \cdot \frac{Q_{bk} - Q_b}{Q_{bk} - Q_{b1}}$$

for $$Q_b < Q_{bk}.$$

30. The device according to claim 16, wherein the blood constituent is haemoglobin.

31. An apparatus for extracorporeal blood treatment, the apparatus comprising:
- an extracorporeal blood circuit comprising a venous hose line and an arterial hose line;
- a dialysing fluid system; and
- the determining device for determining the concentration of the blood constituent according to claim 16.

* * * * *